(12) United States Patent
Dolphin et al.

(10) Patent No.: US 10,238,603 B2
(45) Date of Patent: Mar. 26, 2019

(54) GELATIN/PECTIN PARTICLES

(71) Applicant: GELITA AG, Eberbach (DE)

(72) Inventors: John M. Dolphin, Sioux City, IA (US); Michelle A. Montgomery, Dakota Dunes, SD (US)

(73) Assignee: GELITA AG, Eberbach (DE)

( * ) Notice: Subject to any disclaimer, the term of this patent is extended or adjusted under 35 U.S.C. 154(b) by 0 days.

(21) Appl. No.: 15/428,793

(22) Filed: Feb. 9, 2017

(65) Prior Publication Data
US 2017/0151176 A1 Jun. 1, 2017

Related U.S. Application Data

(63) Continuation of application No. PCT/EP2015/066663, filed on Jul. 21, 2015.

(60) Provisional application No. 62/049,034, filed on Sep. 11, 2014.

(51) Int. Cl.
| | |
|---|---|
| *A61K 9/16* | (2006.01) |
| *A23L 29/30* | (2016.01) |
| *A23L 21/00* | (2016.01) |
| *A61K 9/48* | (2006.01) |
| *A23P 10/20* | (2016.01) |
| *A23L 29/231* | (2016.01) |
| *A23L 29/281* | (2016.01) |

(52) U.S. Cl.
CPC ............ *A61K 9/1658* (2013.01); *A23L 21/00* (2016.08); *A23L 29/231* (2016.08); *A23L 29/284* (2016.08); *A23L 29/30* (2016.08); *A23P 10/20* (2016.08); *A61K 9/1623* (2013.01); *A61K 9/1652* (2013.01); *A61K 9/1694* (2013.01); *A61K 9/4816* (2013.01); *A61K 9/4825* (2013.01); *A23V 2002/00* (2013.01)

(58) Field of Classification Search
CPC ... A23L 29/231; A23L 29/284; A61K 9/1658; A61K 9/1694; A61K 9/4825
See application file for complete search history.

(56) References Cited

U.S. PATENT DOCUMENTS

| | | | | | |
|---|---|---|---|---|---|
| 5,558,071 | A * | 9/1996 | Ward | ......................... | F02P 3/02 123/598 |
| 5,928,706 | A * | 7/1999 | Gibson | ..................... | A21D 2/08 424/489 |
| 6,579,851 | B2 * | 6/2003 | Goeke | ..................... | A61K 38/26 514/11.7 |
| 7,041,315 | B2 * | 5/2006 | Scott | ..................... | A61K 8/0216 424/451 |
| 8,461,129 | B2 * | 6/2013 | Bolduc | ................... | A61L 15/28 127/49 |
| 8,962,005 | B2 | 2/2015 | Chidambaram | | |
| 9,192,582 | B2 | 11/2015 | Chidambaram | | |
| 2011/0028412 | A1 * | 2/2011 | Cappello | ............ | A61K 31/7004 514/25 |
| 2013/0041004 | A1 * | 2/2013 | Drager | ..................... | A61K 9/08 514/394 |
| 2013/0084243 | A1 * | 4/2013 | Goetsch | ............. | C07K 16/2863 424/1.49 |
| 2013/0096073 | A1 * | 4/2013 | Sidelman | ........... | A61K 38/1709 514/21.6 |
| 2013/0259933 | A1 | 10/2013 | Kamaguchi et al. | | |
| 2014/0072625 | A1 | 3/2014 | Chidambaram | | |
| 2015/0174076 | A1 * | 6/2015 | Harris | ..................... | A61K 9/006 424/489 |

FOREIGN PATENT DOCUMENTS

| | | | | | |
|---|---|---|---|---|---|
| CN | 102415465 A | * | 4/2012 | | |
| DE | 203 17 204 U1 | | 3/2004 | | |
| EP | 0 888 778 A1 | | 1/1999 | | |
| EP | 0888778 A1 | * | 1/1999 | ............ | A61K 9/286 |
| EP | 1 184 033 A1 | | 3/2002 | | |

OTHER PUBLICATIONS

Machine translation of Zhang (CN102415465), 2018, pp. 1-7 (Year: 2018).*
Joseph, I. et al. "Indomethacin sustained release from alginate-gelatin or pectin -gelatin coacervates" International Journal of Pharmaceutics 126 (1995) 161-168 (Year: 1995).*
GMIA "Gelatin Handbook" Gelatin Manufacturers Institute of America, Jan. 2012, pp. 1-25 (Year: 2012).*
Saravanan, M. et al. "Pectin—gelatin and alginate—gelatin complex coacervation for controlled drug delivery: Influence of anionic polysaccharides and drugs being encapsulated on physicochemical properties of microcapsules" Carbohydrate Polymers 80 (2010) 808-816 (Year: 2010).*
International Bureau, International Preliminary Report on Patentability in International Patent Application No. PCT/EP2015/066663, dated Mar. 23, 2017.
International Bureau, International Preliminary Report on Patentability in International Patent Application No. PCT/EP2015/066663, dated Sep. 29, 2015.
International Bureau, International Search Report in international Patent Application No. PCT/EP2015/066663, dated Sep. 29, 2015.
Ishmael et al., "Indomethacin sustained release from alginate-gelatin or pectin-elatin coacervates," *International Journal of Pharmaceutics*, 126: 161-168 (1995).

(Continued)

*Primary Examiner* — Andrew S Rosenthal
(74) *Attorney, Agent, or Firm* — Leydig, Voit & Mayer

(57) ABSTRACT

Disclosed are particles comprising pectin and gelatin. The particles may be useful for preparing any of a variety products such as, for example, soft pharmaceutical capsules, hard pharmaceutical capsules, and foodstuffs. Also disclosed are methods for preparing the particles, the method comprising: (a) dissolving pectin in an aqueous solution to produce an aqueous solution of dissolved pectin; (b) mixing the aqueous solution of dissolved pectin with liquid gelatin to produce a gelatin/pectin mixture; (c) drying the gelatin/pectin mixture; and (d) milling the gelatin/pectin mixture to produce the plurality of particles.

21 Claims, No Drawings

(56) References Cited

OTHER PUBLICATIONS

McMullen et al., "Pectin-gelatin complex coacervates I: Determinants of microglobule size, morphology, and recovery as water-dispersible powders," *Journal of Pharmaceutical Sciences*, 71(6); 628-633 (1982).
Product literature, GENU Family of Pectin, "Guidelines for Proper Dissolution" (available by Aug. 5, 2014).
TIC GUMS product literature, TIC Pretested® Agar Agar 100 FCC/NF Powder, available by Aug. 28, 2014.

\* cited by examiner

GELATIN/PECTIN PARTICLES

CROSS-REFERENCE TO RELATED APPLICATIONS

This patent application is a Continuation of international Patent Application No. PCT/EP2015/066663, filed Jul. 21, 2015, which claims the benefit of U.S. Patent Application No. 62/049,034, filed Sep. 11, 2014, which are each incorporated herein by reference.

BACKGROUND OF THE INVENTION

A hydrocolloid, such as pectin, should be dissolved in solution in order for the hydrocolloid to be useful for preparing any of a variety products such as, for example, hard pharmaceutical capsules, soft pharmaceutical capsules, and foodstuffs. However, the procedures for dissolving the hydrocolloid can be time-consuming, cumbersome, and laborious. For example, in order to achieve dissolution of the hydrocolloid pectin, the temperature of the pectin solution should reach at least 80° C., and in some cases, boiling is recommended. Vigorous agitation, such as with a high-shear mixer, may also be highly recommended by pectin producers in order to ease solution preparation.

Accordingly, there is a need for improved gelatin/pectin compositions.

BRIEF SUMMARY OF THE INVENTION

An embodiment of the invention provides a particle comprising pectin and gelatin.

Another embodiment of the invention provides a particle consisting of (a) water, (b) pectin, (c) gelatin, (d) optionally one or more carbohydrates, (e) optionally one or more organic acids or salt(s) thereof, and (f) optionally one or more inorganic salts.

An embodiment of the invention provides a method of making a plurality of the particles, the method comprising: (a) dissolving pectin in an aqueous solution to produce an aqueous solution of pectin; (b) mixing the aqueous solution of dissolved pectin with liquid gelatin to produce a gelatin/pectin mixture; (c) drying the gelatin/pectin mixture; and (d) milling the gelatin/pectin mixture to produce the plurality of particles.

DETAILED DESCRIPTION OF THE INVENTION

An embodiment of the invention provides a particle comprising pectin and gelatin. The particle provides many advantages, particularly when the particle is used to prepare products that contain pectin and gelatin such as, for example, soft pharmaceutical capsules, hard pharmaceutical capsules, and foodstuffs (hereinafter, "pectin-gelatin end products"). For example, because the inventive particle advantageously and surprisingly provides the same or similar dissolution properties as gelatin alone, the particle advantageously makes it possible to avoid the step of pre-dissolving the pectin prior to combining the pectin with the gelatin in a method of preparing pectin-gelatin end products. In this regard, the inventive particle makes it possible to avoid the time-consuming, cumbersome, and laborious aspects of pre-dissolving the pectin such as, for example, any one or more of adding the pectin slowly to the aqueous solution; holding the mixture of pectin and aqueous solution at a high temperature (such as, for example about 85° C.) for a lengthy period of time (for example, two hours); vigorous agitation to, for example, prevent clumping (such as with a high-shear mixer); and cooling the mixture to, for example, about 60° C. to about 65° C. With the inventive particles, methods of preparing pectin-gelatin end products use fewer pieces of equipment and are faster, simpler, and less expensive as compared to methods of preparing pectin-gelatin end products that use pectin (that does not contain gelatin) and gelatin (that does not contain pectin) as starting materials.

The particle may have any suitable shape and size. In an embodiment, the particle is a granule. In an embodiment, the particle has a size of from about 6 mesh (about 3.0 mm) to about 40 mesh (about 0.4 mm), preferably from about 6 mesh (about 3.4 mm) to about 16 mesh (about 1.2 mm).

The particle may comprise any suitable amount of pectin. In an embodiment of the invention, the pectin is present in an amount of from about 1% to about 30% by weight (in relation to dry mass) of the particle, preferably from about 5% to about 15% by weight (in relation to dry mass) of the particle.

In an embodiment of the invention, the pectin comprises any one or more of low methoxyl (LM) pectin, high methoxyl (HM) pectin, amidated high methoxyl pectin, and amidated low methoxyl pectin. "Low methoxyl pectin," as used herein, means pectin in which less than 50% of the carboxyl acid units occur as methyl esters. "High methoxyl pectin," as used herein, means pectin in which 50% or more of the carboxyl groups occur as methyl esters.

The particle may comprise any suitable amount of gelatin. In an embodiment of the invention, the gelatin is present in an amount of from about 70% to about 99% by weight (in relation to dry mass) of the particle, preferably from about 85% to about 95% by weight (in relation to dry mass) of the particle.

The gelatin may be any suitable gelatin. In an embodiment of the invention, the gelatin comprises type B gelatin, type A gelatin, or a combination thereof. Examples of type B gelatin suitable for use in the inventive particles include type B bovine bone gelatin and type B bovine hide gelatin. An example of type A gelatin suitable for use in the inventive particles is type A porcine skin gelatin. The gelatin of the particles may have any suitable bloom range. In an embodiment, the gelatin has a bloom range of from about 50 to about 300, preferably from about 70 to about 180.

In an embodiment of the invention, it may be advantageous to add additional inorganic salts of multiple charged cations (e.g. $Ca^{2+}$ or $Mg^{2+}$) to the particles in order to facilitate gelling of the pectin. In this regard, in an embodiment of the invention, the particle comprises inorganic salts of multiple charged cations. The particle may have an inorganic salt of a multiple charged cation content of greater than about 100 parts per million with respect to the particle. In an embodiment of the invention, it may be advantageous to minimize inorganic salts of multiple charged cations (e.g. $Ca^{2+}$ or $Mg^{2+}$) in the particles in order to impede gelling of the pectin and facilitate dissolution of the gelatin/pectin particles. In this regard, in an embodiment of the invention, the particle contains very low levels of inorganic salts of multiple charged cations. The particle may have an inorganic salt of multiple charged cation content of less than 100 parts per million with respect to the particle. In an embodiment of the invention, the particle contains no inorganic salts of a multiple charged cation.

In an embodiment of the invention, the particle further comprises one or more carbohydrates. In an embodiment, the one or more carbohydrates comprise(s) one or both of maltodextrin and a sugar. The sugar may be any suitable sugar(s). Examples of suitable sugars include, but are not limited to, one or more of sucrose, glucose, and maltose. In an embodiment of the invention, the one or more carbohydrate(s) is/are present in an amount of about 5% or less by weight (in relation to dry mass) of the particle. In an embodiment of the invention, the particle contains no carbohydrates.

In an embodiment of the invention, the particle further comprises one or more organic acids or salt(s) thereof. In an embodiment, the one or more organic acids or salt(s) thereof comprise(s) one or more of lactic acid, acetic acid, formic acid, citric acid, oxalic acid, uric acid, malic acid, a carboxylic acid, a sulfonic acid, and salt(s) thereof. In an embodiment of the invention, the one or more organic acids or salt(s) thereof is/are present in an amount of about 5% or less by weight (in relation to dry mass) of the particle. In an embodiment of the invention, the particle contains no organic acids or salt(s) thereof.

In an embodiment of the invention, the particle further comprises one or more inorganic salts. In an embodiment, the one or more inorganic salts comprise(s) one or more of sodium chloride, potassium chloride, calcium chloride, magnesium chloride, sodium sulfate, potassium sulfate, calcium sulfate, magnesium sulfate, sodium phosphates, potassium phosphates, calcium phosphates, magnesium phosphates, sodium nitrate, potassium nitrate, calcium nitrate, and magnesium nitrate. In an embodiment of the invention, the one or more inorganic salts is/are present in an amount of about 5% or less by weight (in relation to dry mass) of the particle. In an embodiment of the invention, the particle contains no inorganic salts.

The particle may further comprise water. The particle may comprise any suitable amount of water. In an embodiment, the water is present in an amount of about 5% to about 15% by weight (in relation to dry mass) of the particle.

In an embodiment of the invention, the particle consists of, or consists essentially of, (a) water, (b) pectin, (c) gelatin, (d) optionally one or more carbohydrates, (e) optionally one or more organic acids or salt(s) thereof, and (f) optionally one or more inorganic salts. The amounts and types of pectin, gelatin, carbohydrate(s), organic acid(s) or salt(s) thereof, inorganic salt(s) may be as described herein with respect to other aspects of the invention. In an embodiment of the invention, the inorganic salt is a calcium salt.

Another embodiment of the invention provides a plurality of any of the particles described herein.

The particle advantageously and surprisingly provides the same or similar dissolution properties as gelatin alone. In an embodiment of the invention, the particle dissolves in water at ≤60° C. In an embodiment of the invention, the particle dissolves in a mixture of water and at least one plasticizer at ≤60° C. The plasticizer may be any suitable plasticizer for preparing pectin/gelatin compositions. In an embodiment, the plasticizer is glycerol, sorbitol, sorbitan, mannitol, or any combination thereof. The plasticizer may be present in the mixture in any suitable amount. In an embodiment, the plasticizer is present in an amount from about 5% to about 40% by weight of the total amount of the mixture.

Still another embodiment of the invention provides a method of making the plurality of particles. The method may comprise dissolving pectin in an aqueous solution to produce an aqueous solution of dissolved pectin. The amount of pectin to be dissolved in the aqueous solution and the amount of aqueous solvent may be determined by the skilled artisan. For example, the aqueous solution of dissolved pectin may comprise about 0% to about 20% pectin and about 80% to about 100% solvent. The method may further comprise dissolving any one or more carbohydrate(s), organic acid(s) or salts thereof, and inorganic salt(s) in the aqueous solution of dissolved pectin. The one or more pectin, carbohydrate(s), organic acid(s) or salts thereof, and inorganic salt(s) may be as described herein with respect to other aspects of the invention.

The dissolving of the pectin in the aqueous solution may be carried out at any suitable temperature. For example, the temperature may be about 80° C. to boiling.

The method may further comprise mixing the aqueous solution of dissolved pectin with liquid gelatin to produce a gelatin/pectin mixture. The amount of liquid gelatin in the mixture of aqueous solution of dissolved pectin and liquid gelatin may be determined by the skilled artisan. For example, the mixture of aqueous solution of dissolved pectin and liquid gelatin may comprise about 70% to about 100% liquid gelatin and about 0% to about 70% aqueous solution of dissolved pectin. The method may further comprise dissolving one or more plasticizers in the mixture of aqueous solution of dissolved pectin and liquid gelatin. The one or more plasticizers may be as described herein with respect to other aspects of the invention.

The mixing of the aqueous solution of dissolved pectin with liquid gelatin may be carried out at any suitable temperature. For example, the temperature may be about 40° C. to about 70° C.

The method may further comprise drying the gelatin/pectin mixture. The drying may be carried out in any suitable manner. For example, the method may comprise cooling the gelatin/pectin mixture and extruding the mixture onto a stainless steel mesh continuous conveyor. The method may comprise carrying the mixture on the conveyer into a dryer. The dryer may be a tunnel containing interior zones or compartments that utilizes dehumidified and heated air in order to remove moisture from the gelatin/pectin mixture. As the mixture passes through the dryer, heated air may be blown through the gelatin/pectin mixture and mesh conveyor to achieve the desired dryness. The dried gelatin/pectin mixture may have any suitable moisture content. For example, the moisture content of the dried gelatin/pectin mixture may be about 5% to about 15%. The drying may be carried out at any suitable temperature. In an embodiment of the invention, the drying is initially carried out at a temperature of about 25° C., and the temperature increases during drying to a temperature of about 54-55° C. at the end of drying.

The method may further comprise milling the gelatin/pectin mixture to produce the plurality of particles. The milling may be carried out in any suitable manner. For example, the milling may comprise breaking the gelatin/pectin mixture into small pieces using equipment adapted for such purpose. The gelatin/pectin mixture may then be carried on a conveyer to a coarse grinder, which further breaks the gelatin/pectin mixture into particles (e.g., granules) of the desired size. The size of the completed, milled granules may be as describes herein with respect to other aspects of the invention.

The following examples further illustrate the invention but, of course, should not be construed as in any way limiting its scope.

EXAMPLE 1

This example demonstrates a method of preparing a gel mass suitable for preparing a soft pharmaceutical capsule using a plurality of particles, wherein each particle comprises gelatin and pectin.

In 57.0 g of deionized water at room temperature, 15.0 g of glycerol (10%) and 18.0 g of plasticizer POLYSORB®85/70/00 (an aqueous solution of D-sorbitol and 1.4-sorbitan obtained by partial internal dehydration of a liquid sorbitol) (12.0%) were dissolved to provide a solution. Then, a plurality of particles, wherein each particle comprises gelatin and pectin (60.0 g) were dispersed in the solution to provide a mixture having 40.0% gelatin/pectin content. The mixture was then heated to 60° C. to dissolve all components. After debubbling, the gel mass viscosity was measured to be 24,320 cP. The process described in this Example took 2-3 hours to complete.

EXAMPLE 2

This example demonstrates a method of preparing a gel mass suitable for preparing a soft pharmaceutical capsule using a plurality of particles, wherein each particle comprises gelatin and pectin.

In 60.0 g of deionized water at room temperature, 30 g of glycerol (20%) was dissolved to provide a solution. Then, a plurality of particles, wherein each particle comprises gelatin and pectin (60.0 g) were dispersed in the solution to provide a mixture having a 40.0% gelatin/pectin content. The mixture was heated to 60° C. to dissolve all components. After debubbling, the gel mass viscosity was measured to be 25,000 cP. The process described in this Example took 2-3 hours to complete.

EXAMPLE 3

This example demonstrates a method of preparing a gel mass suitable for preparing a hard pharmaceutical capsule using a plurality of particles, wherein each particle comprises gelatin and pectin.

In 105 g of deionized water at room temperature, a plurality of particles, wherein each particle comprises gelatin and pectin (45 g) were dispersed to provide a mixture having a 30% gelatin/pectin content. The mixture was heated to 60° C. to dissolve all components. After debubbling, the gel mass viscosity was measured to be 1,840 cP. The process described in this Example took 1-2 hours to complete.

EXAMPLE 4

This example demonstrates a method of preparing gummy candy using a plurality of particles, wherein each particle comprises gelatin and pectin.

A gelling solution was prepared by dissolving a plurality of particles, wherein each particle comprises gelatin and pectin (22.0 g), in 44.0 g of water at 60° C. It took 30 minutes to dissolve the particles. Separately, a mixture of 160.40 g of 42DE corn syrup, 120.80 g of sugar, 26.40 g of sorbitol, and 18.80 g of water was prepared and boiled at 115-125° C. until the solids reached 85-86% Brix. The sugar mixture was cooled to 100° C. The corn syrup/sugar/water mixture was combined with the gelatin/pectin solution plus 7.58 g of citric acid (50% w/w), 0.50 g of coloring ingredients, and 4.2 g of flavoring ingredients. The combination was mixed well, deposited into starch molding, and dried at room temperature for 24 hours. The resulting gummy candies had an average internal texture of 62.7 g and an average water activity of 0.64 after removing them from the molds.

COMPARATIVE EXAMPLE

This example demonstrates a process used by capsule producers to make a gel mass suitable for preparing a non-coated, enteric soft pharmaceutical capsule using (a) pectin powder (that does not contain gelatin) and (b) gelatin film-forming polymer (that does not contain pectin) as starting materials.

The acid-insoluble polymer, pectin, is first dissolved in water. The water is heated to 85° C. and then the pectin powder is slowly added to the water with vigorous agitation to prevent the pectin from clumping. This solution is held at 85° C. for at least two hours to allow all of the pectin to go into solution. Once in solution, the mixture is cooled to 60-65° C. In a second vessel, the film-forming polymer, gelatin, is mixed with plasticizer. This mixture is then added to the pectin solution and heated at 60-65° C. for two hours. The gelatin/pectin gel mass solution is then degassed and colorants are added, if necessary. The enteric gel mass is then ready to be used in an encapsulation process. The process described in this Comparative Example takes 5-7 hours to complete.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A plurality of particles, which are made by a method comprising:
   (a) dissolving pectin in an aqueous solution to produce an aqueous solution of dissolved pectin;
   (b) mixing the aqueous solution of dissolved pectin with liquid gelatin to produce a gelatin/pectin mixture;
   (c) drying the gelatin/pectin mixture; and
   (d) milling the gelatin/pectin mixture to produce the plurality of particles wherein the particles consist of:
      (i) water;
      (ii) pectin;
      (iii) gelatin;
      (iv) optionally one or more carbohydrates;
      (v) optionally one or more organic acids or salt(s) thereof; and
      (vi) optionally one or more inorganic salts.

2. The plurality of particles of claim 1, wherein the pectin is low methoxyl (LM) pectin, high methoxyl (HM) pectin, amidated high methoxyl pectin, or amidated low methoxyl pectin.

3. The plurality of particles of claim 1, wherein the gelatin is type B gelatin.

4. The plurality of particles of claim 1, wherein the gelatin comprise is type A gelatin.

5. The plurality of particles of claim 1, wherein the gelatin has a bloom range of from 50 to 300.

6. The plurality of particles of claim 1, wherein the gelatin has a bloom range of from 70 to 180.

7. The plurality of particles of claim 1, wherein the particles have an inorganic salt of multiple charged cations content of less than 100 parts per million with respect to the particles.

8. The plurality of particles of claim 1, wherein the particles have an inorganic salt of multiple charged cations content of greater than 100 parts per million with respect to the particles.

9. The plurality of particles of claim 1, wherein the pectin is present in an amount of from 1% to 30% by weight (in relation to dry mass).

10. The plurality of particles of claim 1, wherein the pectin is present in an amount of from 5% to 15% by weight (in relation to dry mass).

11. The plurality of particles of claim 1, wherein the gelatin is present in an amount of from 70% to 99% by weight (in relation to dry mass).

12. The plurality of particles of claim 1, wherein the gelatin is present in an amount of from 85% to 95% by weight (in relation to dry mass).

13. The plurality of particles of claim 1, wherein the particles have a size of from 6 mesh to 40 mesh.

14. The plurality of particles of claim 1, wherein the particles have a size of from 6 mesh to 16 mesh.

15. The plurality of particles of claim 1, wherein the one or more carbohydrates is/are present in the particles.

16. The plurality of particles of claim 15, wherein the one or more carbohydrates is/are one or more of maltodextrin, sucrose, glucose, and maltose.

17. The plurality of particles of claim 1, wherein the particles dissolve in water at ≤60° C.

18. The plurality of particles of claim 1, wherein the particles dissolve in a mixture of water and at least one plasticizer at ≤60° C.

19. The plurality of particles of claim 18, wherein the plasticizer is glycerol, sorbitol, sorbitan, mannitol, or any combination thereof.

20. The plurality of particles of claim 18, wherein the plasticizer is present in an amount from 5% to 40% by weight of the total amount of the mixture.

21. A method of making the plurality of particles of claim 1, the method comprising:
   (a) dissolving pectin in an aqueous solution to produce an aqueous solution of dissolved pectin;
   (b) mixing the aqueous solution of dissolved pectin with liquid gelatin to produce a gelatin/pectin mixture;
   (c) drying the gelatin/pectin mixture; and
   (d) milling the gelatin/pectin mixture to produce the plurality of particles.

* * * * *